United States Patent [19]

Johnson, Jr.

[11] 4,287,920

[45] Sep. 8, 1981

[54] SELF-SEALING VALVE

[76] Inventor: Glenn W. Johnson, Jr., 10 Friar Tuck Cir., Summit, N.J. 07901

[21] Appl. No.: 59,746

[22] Filed: Jul. 23, 1979

Related U.S. Application Data

[63] Continuation-in-part of Ser. No. 842,961, Oct. 17, 1977, abandoned.

[51] Int. Cl.³ ............................................. B65B 3/17
[52] U.S. Cl. ................................... 141/85; 53/570; 141/313
[58] Field of Search ................... 46/90; 128/DIG. 24, 128/214 D, 272; 141/10, 114, 98, 313–317, 329, 85; 150/9; 229/48 SB, 62, 62.5; 53/570; 137/223, 237, 246

[56] References Cited

U.S. PATENT DOCUMENTS

| | | | |
|---|---|---|---|
| 3,307,773 | 3/1967 | Kratzer et al. | 229/48 SB |
| 3,523,563 | 8/1970 | Mirando | 46/90 X |

*Primary Examiner*—Frederick R. Schmidt

[57] ABSTRACT

A fluid-filled or inflatable article having an integral self-sealing valve formed from a pair of extensions which are sealed together along their peripheral side edges leaving an open top or mouth. One or both of the extensions is folded back upon itself to form a flap or pair of juxtaposed flaps whose free edge or edges depend inwardly from the open top or mouth of the valve. Disposed between the flaps, or between the flap and the adjacent inner surface of the opposed valve wall if a single flap is employed, is a biasing means preferably in the form of a thin layer of a tacky, grease-like substance which causes the flaps to adhere to each other or to the inner side wall of the adjacent opposed valve wall thereby biasing the flap into sealing engagement with each other or the adjacent inner wall surface interiorly of the valve. This action enhanced by the back pressure of the fluid inside the inflated article causes the flap to be maintained in a fluid-tight sealing engagement against the other flap or against the confronting inner surface of the valve wall thus sealing the mouth of the valve in a leak-proof manner.

4 Claims, 8 Drawing Figures

SELF-SEALING VALVE

This application is a continuation-in-part of copending application, Ser. No. 842,961, filed Oct. 17, 1977, now abandoned.

The present invention relates generally to self-sealing valves and more particularly to self-sealing valves for fluid-filled or inflatable articles.

In my prior U.S. Pat. No. 3,955,565 there is fully disclosed an orthopedic apparatus comprising a pair of complementary, semi-rigid plastic half-shell members which are radially telescoped relative to each other to form an outer casing for a plurality of pneumatic cells or inflatable airbags. One known valve construction which may be used to maintain the internal pressure of the airbags in such apparatus consists of a single pin stopper inserted into the inlet tube of each airbag immediately upon inflation to a desired internal pressure. However, this involves separate parts capable of being lost, dexterity in manipulating the pin stopper so as to properly fit it into the relatively small inlet tube (i.e., a diameter on the order of ⅛" O.D.,) and the relatively high cost of manufacturing the separate pin stoppers.

Still another known form of valve construction for inflatable airbags, disclosed in U.S. Pat. No. 3,230,663 to Shabram, consists of a funnel-like extension integral with the airbag and having an opening in which is disposed an inwardly folded flap adapted to close off the opening in response to the internal or back pressure of the airbag. As the Shabram patent points out in column 2, line 16 et seq., the inflatable article and integral valve disclosed therein are fabricated from two sheets of plastic material heat-sealed together with the best thickness of the material being about two mils. In addition, the Shabram patent discloses in connection with FIG. 22 thereof, that inflation of the article is carried out by employing the user's fingers to press inwardly from the opposed seams of the valve which results in the valve opening to permit manual inflation of the article.

Unfortunately, it has been found that when the Shabram valve is used in connection with inflatable airbags fabricated from sheets of a plastic material e.g., vinyl) whose thickness is appreciably greater than two mils, say, in the range of 10 to 30 mils as required in a high reliability orthopedic device, it is virtually impossible to open the valve via manipulations of one's fingers and therefore, some other method not disclosed in Shabram must be used to inflate the article. Moreover, it has been found that when the Shabram valve is used in connection with the expected high reliability airbags of the orthopedic apparatus disclosed in my prior patent cited above; that is, where the material of the airbag is a vinyl plastic having a thickness in the range of say 10 to 20 mils, and an internal or back pressure of from 15 to about 25 mm Hg., the valve is prone to leakage.

Against the foregoing background, it is an object of the present invention to provide a self-sealing valve for a fluid-filled or inflatable article that is leak-proof and relatively inexpensive to fabricate.

It is still another object of the present invention to provide an improved valve for an inflatable article over that disclosed in Shabram U.S. Pat. No. 3,230,663.

It is yet another object of the present invention to provide a novel method of opening the self-closing valve of the type disclosed in Shabram U.S. Pat. No. 3,230,663, and of inflating the article thereof without the necessity of employing one's fingers to manipulate the valve by pressing inwardly from the valve's opposed seams.

Toward the accomplishment of these and additional objects and advantages, the present invention comprises, in brief summary, a fluid-filled or inflatable article having an integral self-sealing valve formed from a pair of extensions which are sealed together along their peripheral side edges leaving an open top or mouth. One or both of the extensions is folded back upon itself to form a flap or pair of juxtaposed, confronting flaps whose free edge or edges depend inwardly from the open top or mouth of the valve. Disposed between the flaps, or between the flap and the confronting inner surface of the opposed valve wall if a single flap is employed, is a biasing means preferably in the form of a thin layer of a tacky, grease-like substance which causes the flaps to adhere to each other or to the side wall surface of the confronting valve wall thereby biasing the flap into sealing engagement with each other or the confronting wall surface interiorly of the valve. This action enhanced by the back pressure of the fluid inside the inflated article causes the flap to be maintained in a fluid-tight sealing engagement against the other flap or against the opposed inner side surface of the valve wall thus sealing the mouth of the valve in a leak-proof manner.

The grease-like substance may be introduced into the throat of the valve after fabrication of the inflatable article by any suitable means such as dispensing it through the tubular nozzle of a metering pump or transferring it from the end of a plastic tube similar to that employed for inflation. After placing a small quantity of the grease-like substance in the throat of the valve, a slight rubbing pressure against the exterior side wall surfaces of the valve is normally sufficient to spread a thin layer of the grease-like substance along the mutually confronting surfaces of the flaps or between a flap and the confronting wall surface of the valve as the case may be, thus preparing the valve to be biased into a sealed condition. Inflation of the article may then be accomplished by inserting a small hollow tube into the throat of the valve and blowing via mouth pressure through the other end of the tube.

The foregoing and still other features and advantages as well as a more complete understanding of the present invention will be made apparent from a study of the following detailed description of the invention in connection with the accompanying drawings wherein.

Figure 1:
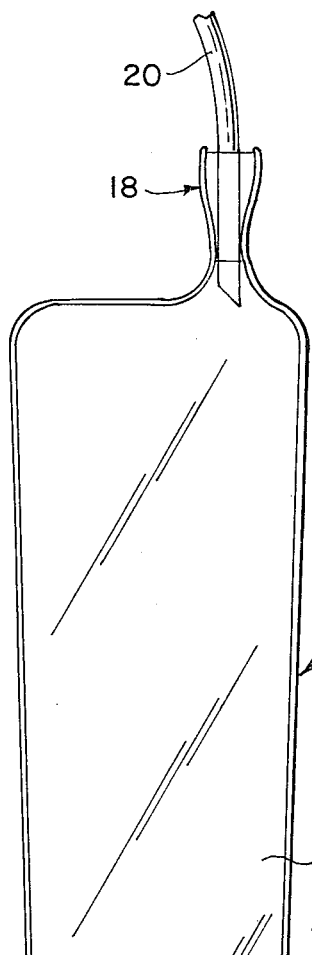
FIG. 1 is a view in elevation of an inflatable article incorporating the self-sealing valve of the present invention and showing an air-inlet tube inserted within the valve in accordance with the method of the present invention.

Turning now to FIG. 1, there is shown an inflatable article generally designated by reference numeral 10 in the form of an elongate pneumatic cell or airbag which may be used in the orthopedic apparatus disclosed in my prior U.S. Pat. No. 3,955,565, which patent is hereby incorporated herein by this reference. As taught in the '565 patent, a plurality of such airbags may be confined in place against a body part (e.g., the lower leg of a human) by an encasement comprised of a pair of semi-rigid, plastic, half-shell members radially telescoped together. As further taught in the '565 patent, the airbags substantially line the interior of the half-shell members and preferably, are inflated to a supporting pressure after the half-shell members have been telescopingly fitted relative to each other and snugly secured in place about a limb or other body part.

Thus, in the preferred form shown in FIG. 1, airbag 10 includes an upper portion 12 which, for example, may be disposed against the shin bone region of the lower leg, and a lower portion 14 which, for example, may be disposed against the instep portion of the foot. Upper portion 12 is joined to lower portion 14 through a necked-down portion 16 which facilitates flexual movement of the lower portion relative to the upper portion when the airbag 10 is inflated.

A self-sealing valve according to the present invention and generally represented by reference numeral 18 is integrally joined to the upper portion 12 substantially as shown for permitting a pressurizing fluid (i.e., air) to be introduced into the interior of airbag 10 and for maintaining the internal pressure of the airbag at a predetermined level. As will be explained in greater detail hereinafter, a separate, hollow inlet tube 20 is adapted to be inserted into valve 18 for facilitating opening of the valve and inflation of the airbag.

Turning to FIGS. 2-5, valve 18 in a first preferred form comprises coextensive, opposed wall portions 22, 24 which are integral extensions of the respective opposed side walls of airbag upper portion 12. Each wall portion 22, 24 is folded inwardly upon itself to form a pair of folds 26, 28 defining the opening or mouth of valve 18 and a further pair of confronting inner wall portion extensions or flaps 30, 32 the distal edges of which terminate within the throat of the valve as at 34, 36, respectively.

In fabricating the airbag 10 and its integral valve 18, the same method may be used as that disclosed in the Shabram Pat. No. 3,230,663 which latter patent is also incorporated herein by reference. Thus, two sheets of pliable plastic material such as, for example, vinyl plastic having a thickness of approximately 12 mils, are first cut to a shape sufficient to form the airbag and integral valve substantially as shown in FIG. 1. The extensions forming the valve wall portions are folded in place to form the confronting flaps 30, 32 and the two sheets coextensively superimposed relative to each other whereupon they are heat-sealed or otherwise bonded together along their peripheral edges to form a continuous seam 38 terminating on either side of the opening or mouth of valve 18 formed by folds 26, 28. It will be appreciated that seam 38 seals the corresponding lateral edges of the valve wall portions 22, 24 and flaps 30, 32 thus forming a pair of pockets 40, 42 opening into the interior of the airbag. It will be appreciated that the back pressure of the fluid inside the airbag will manifest itself within each pocket 40, 42 to urge the inwardly facing or confronting flaps 30, 32 against one another in a manner tending to seal off the valve.

Figure 2:
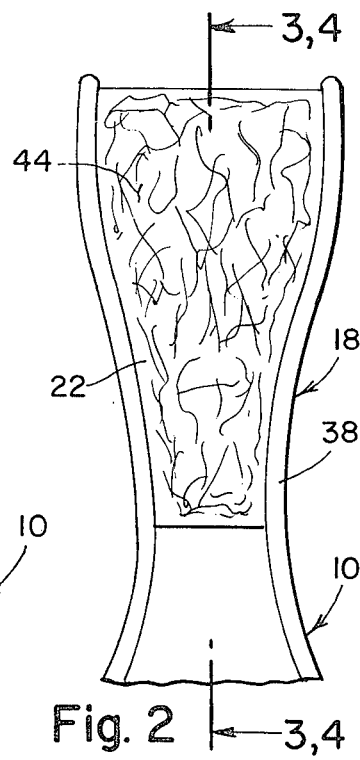
FIG. 2 is an enlarged, fragmentary view of FIG. 1 showing the valve of the present invention in greater detail without the inlet tube inserted therein.

As shown in FIG. 2, the throat of valve 18 tapers outwardly from its narrowest transverse dimension which is located at a point approximately coincidental with the distal edges 34, 36 of flaps 30, 32 until reaching the relatively wider mouth of the valve defined by folds 26, 28. The mouth of the valve is advantageously made wider in this manner so as to facilitate entry of inlet tube 20 as will be made more apparent.

It will be understood that it is not necessary for the distal edges 34, 36 of the inner flaps 30, 32 to be coincidentally aligned with each other and/or the narrowest dimension of the throat of the valve. That is, the inner flaps may be terminated slightly above or below each other, or slightly below or above the narrow throat portion of the valve without adverse effect.

Thus far the construction of valve 18 is essentially similiar to that disclosed in the Shabram patent '663. However, I have found to my surprise that in accordance with the present invention, a significant improvement over the Shabram valve may be achieved by disposing a thin layer or film 44 of a tacky, grease-like substance on either or both inwardly facing surfaces of the confronting inner wall portion extensions or flaps 30, 32. This may be accomplished after fabrication of the article 10, preferably by dispensing the tacky, grease-like substance into the throat of the valve, i.e., between flaps 30, 32, through the tubular nozzle of a conventional metering pump inserted therein. Alternatively, the tacky, grease-like substance may be transferred to the throat interior surfaces via the end of a plastic tube inserted therein such as that employed to inflate the article as will be explained below. After a relatively small quantity of the tacky, grease-like substance has been placed within the interior throat region of the valve, a slight rubbing pressure applied against the exterior side wall surfaces of the valve normally will be sufficient to spread the required thin layer 44 along and between the mutually confronting surfaces of flaps 30, 32.

It is believed that the thin layer 44 of tacky, grease-like substance serves to displace any air trapped between the inwardly facing surfaces of the flaps and causes these surfaces to adhere to one another thereby biasing the valve into a closed or sealed condition especially when a slight rubbing pressure is exerted on the exterior opposed wall portion extensions 22, 24 by the user's thumb and forefinger substantially immediately after desired inflation of the airbag. The back pressure of the fluid within the airbag interior acting within pockets 40, 42 serves to maintain the biased inner flaps in a sealed condition.

The particular tacky, grease-like substance used to establish the thin layer 44 should be sufficiently adherent, have an easily spreadable consistency, avoid any tendency to attack or otherwise adversely affect the vinyl plastic material of the airbag, and be able to maintain its stability over extended periods of time and under varying conditions of temperature, humidity and so on. I have found that a particularly suitable substance meeting these requirements is a silicone-based grease compound readily available under the trademark Dow Corning 11.

In order to verify the surprising, unexpected results afforded by the present invention, an actual test was performed utilizing the airbag and valve described above wherein the airbag had the following dimensions measured in inches within the plane of FIGS. 1 and 2:

| | |
|---|---|
| Length excluding valve: | 16.5 |
| Top width: | 4.0 |
| Bottom width: | 2.75 |
| Wall thickness: | .012 | and wherein the integral self-sealing valve had the following dimensions measured in inches within the plane of FIGS. 1 and 2:

| | |
|---|---|
| Length: | 2.0 |
| Throat: | .312 |
| Mouth: | .625 |
| Distance between mouth and throat: | 1.250 |

The airbag, but without a thin layer 44 of silicone-based grease (Dow Corning 11) applied therein in accordance with the present invention, was inflated by mouth through a hollow tube inserted into the throat of the valve and the valve was allowed to self-close utilizing slight rubbing contact of the thumb and forefinger on the opposed exterior walls of the valve and the back pressure of the air inside the airbag. The inflated airbag then was laid on its side on a table and a 5 pound weight was placed on the upwardly facing side of the inflated airbag. Periodic visual inspection of the airbag over a period of one to six hours revealed gradual vertical downward displacement of the weight relative to the table top surface thus indicating leakage through the valve. Confirmation of leakage was obtained by submerging the inflated airbag into a pan of water and observing air bubbles issuing through the valve.

The same airbag was then treated with an application of a thin layer 44 of silicone-based grease compound (Dow Corning 11) on the inwardly facing surfaces of the valve flaps 30, 32 followed by slight rubbing pressure by the thumb and forefinger on the exterior, opposed walls of the valve. The above test was then repeated. After a period of 10 days, no vertical downward displacement of the 5 pound weight was noted and no bubbles were observed issuing from the valve after water submersion.

Figure 5:
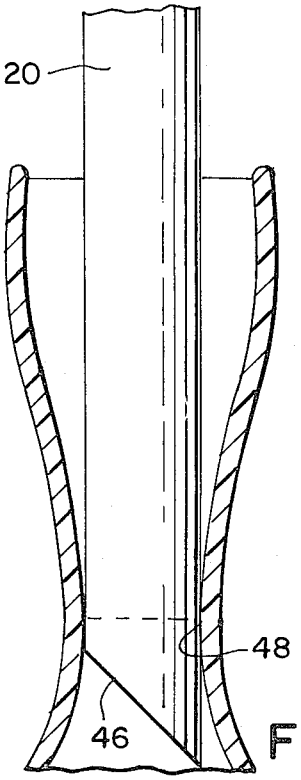
FIG. 5 is an enlarged, fragmentary, sectional view of FIG. 1 showing the valve of the present invention and the air inlet tube inserted within the valve.
Figure 6:
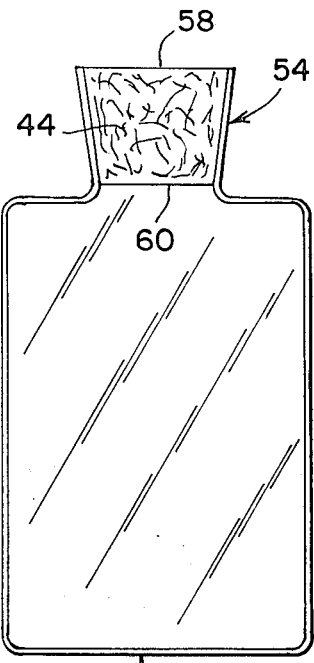
FIG. 6 is a view in elevation of a fluid-fillable article having an alternatively preferred form of self-sealing valve according to the present invention.

In accordance with another aspect of the present invention, opening of the valve 18, and inflation of the airbag may be facilitated by employment of the inlet tube 20 which preferably comprises a short length (e.g., 15-20 inches) of hollow tubing fabricated from a suitable flexible material such as vinyl resin and having an outside diameter or transverse width equal to or slightly less than the narrowest dimension or width of the throat of the valve which narrowest dimension is indicated by the broken line 48 in FIG. 5. By this arrangement, there will be a close or interference fit between the inlet tube and the throat of the valve sufficient to avoid leakage back through the valve during inflation of the airbag. The end of the inlet tube which is to be inserted through the mouth and into the throat of the valve preferably is beveled at 46 to provide a sharpened nose portion which will furthermore facilitate opening of the mouth of the valve and subsequent entry of the inlet tube into and through the valve throat.

The thin layer 44 of tacky, grease-like substance will lubricate the inlet tube thereby permitting easy insertion of the tube into and slightly beyond the narrow throat region of the valve. In the absense of such lubrication, it would be difficult to insert the inlet tube beyond the narrow throat portion of the valve and thereby seal off the valve during inflation due to the close or interference fit between the outside circumference of the inlet tube and the narrow throat dimension of the valve as mentioned above and as indicatedat reference numeral 48 in FIG. 5. In addition, the grease-like substance will aid in limiting leakage back through the valve during inflation in the event there is any clearance between the inlet tube circumference and the throat of the valve.

After the inlet tube has been placed into its proper inflating position as shown in FIG. 5, the interior of the tube may be filled with pressurized air simply by blowing through the other end of the tube 20 (not shown) and then withdrawing the inlet tube from the throat and mouth of the valve while substantially simultaneously applying a slight rubbing contact with the thumb and forefinger to the exterior side wall extensions 22, 24 of the valve, respectively. This will assure that the thin film 44 of the tacky grease-like substance is properly applied between the opposed, mutually confronting surfaces of the inner flaps 30, 32 so as to bias the valve automatically into a self-sealing condition which latter will be maintained by the back pressure of the internal pressurizing fluid acting within pockets 40, 42 to urge the flaps into sealing engagement with each other thereby preventing leakage through the valve.

Figures 3, 4:
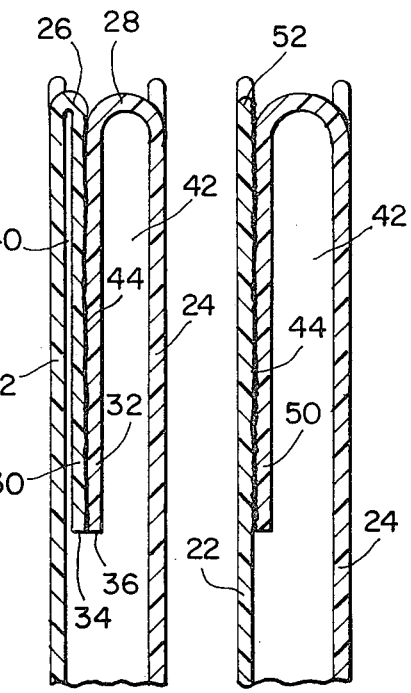
FIG. 3 is a sectional view taken along line 3—3 of FIG. 2.
FIG. 4 is a sectional view taken along line 4—4 of FIG. 2 and showing an alternatively preferred embodiment of the valve of the present invention.

It will be appreciated that many modifications and alterations within the spirit and scope of my invention may be made without departing from the principles disclosed herein. For example, instead of using a pair of inwardly extending flaps 30, 32, a single inwardly folded flap or side wall extension 50 may be employed instead as shown in FIG. 4. Under these circumstances and as depicted in FIG. 4, the thin layer 44 of the tacky, grease-like substance will be applied between the flap 50 and the confronting surface of the opposed side wall extension 22 with the side wall extension 22 terminating at the mouth of the valve at edge 52. In this alternatively preferred embodiment of FIG. 4, sealing of the valve is maintained by the back pressure of the internal pressurizing fluid acting within the pocket 42 to urge flap 50 firmly and securely against the confronting, interior surface of side wall extension 22.

In addition, it is not essential that the valve of the present invention be used with an airbag suitable for use in the orthopedic apparatus of my prior patent '565. Thus, for example, by making the transverse dimensions of the mouth and of the throat of the valve larger and by making the narrow throat dimension larger with respect to the transverse dimension of the mouth of the valve, the latter may function as the self-sealing valve 54 of an ice bag generally represented by reference numeral 56. That is, because of the relatively wide transverse dimensions of the mouth 58 and the throat 60 of the ice bag 56, ice cubes may easily be inserted into the bag. Then, when the layer 44 of tacky, grease-like substance is applied in the manner described above to the confronting surfaces of the valve flap or flaps, the valve may be biased into a closed condition. All of the while, the back pressure of the water produced by the gradually melting ice cubes will help to maintain the valve closed in the same manner described above with respect to the airbag of FIGS. 1-5, and leakage of water through the valve will be avoided.

Referring again to the preferred embodiment of my invention shown in FIGS. 1-5, repeated inflation and deflation of the airbag as by inserting tube 20 many different times into the throat of the valve in the manner described above may gradually cause removable displacement of the thin layer 44 of tacky, grease-like substance from the throat region of the valve i.e., some of the tacky, grease-like substance may adhere to the tube 20 or be pushed downwardly beyond the narrowest transverse dimension of the throat of the valve. In order to avoid this occurrence, means may be provided in the throat of the valve to avoid migration of the tacky, grease-like substance therefrom thus maintaining an adequate supply of the tacky, grease-like substance sufficient to form the thin layer 44 in the valve throat in accordance with the present invention despite a great number of repeated cycles of inflation followed by deflation via insertable tube 20 or similar instrumentality.

Figure 7:
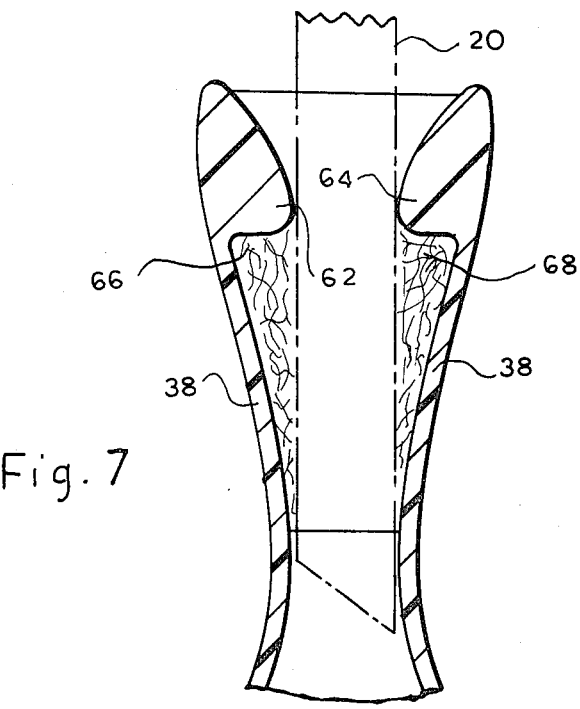
FIG. 7 is an enlarged fragmentary view of an alternatively preferred embodiment of FIGS. 1-5.

In FIG. 7, there is shown an alternatively preferred embodiment of the invention including such migration avoidance means in the form of a pair of opposed inwardly tapered, confronting sections 62, 64 integral with heat-sealed seam 38 each of which defines a corresponding undercut or recess 66, 68 substantially as shown. The inwardly facing extremities of sections 62, 64 preferably are spaced from each other a distance sufficient to permit the passing of tube 20 therethrough, yet to form a temporary seal when tube 20 is in the position shown during entubation or inflation of the airbag. Moreover, the undercuts or recesses 66, 68 being spaced axially above the narrowest transverse dimension of the valve throat forms reservoirs or pockets which because they are positioned laterally or transversely with respect to the tube 20 and its path of axial travel receivably store the tacky, grease-like substance as the tube is repeatedly inserted and withdrawn. The aforesaid means thus function to maintain an adequate supply to form the thin layer 44 after the airbag has been inflated, the tube 20 axially withdrawn, and slight finger pressure has been applied externally to the valve in the region of recesses 66, 68.

Figure 8:
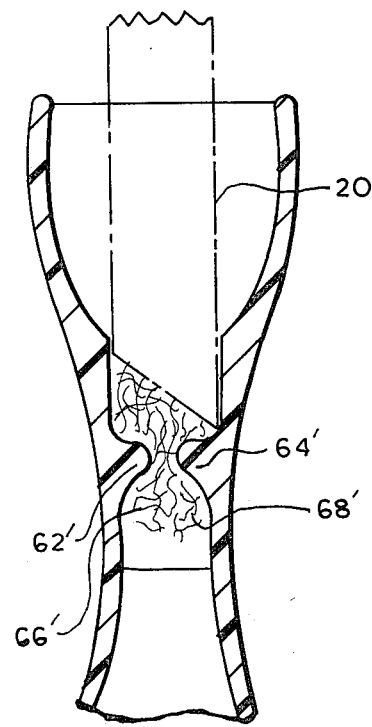
FIG. 8 is an enlarged fragmentary view of yet still another alternatively preferred embodiment of that shown in FIGS. 1-5.

Similar results are achieved by the arrangement shown in FIG. 8 which constitutes yet still another alternatively preferred embodiment of the invention. In the FIG. 8 version substantially as shown, the inwardly extending opposed, confronting sections $62^1$, $64^1$ integral with seam 38 are located proximal to the narrow region of the valve throat and have therein inwardly facing extremities spaced a distance from one another substantially less than the diameter of tube 20 to thus form a stop or barrier limiting axial travel of tube 20. Hence, the tacky, grease-like substance originally deposited into the recesses or pockets $66^1$, $68^1$ formed underneath inwardly extending sections $62^1$, $64^1$ is never disturbed by motion of tube 20.

In the alternatively preferred embodiments of FIGS. 7 and 8, the inwardly extending sections 62, 64, $62^1$, $64^1$ integral with seam 38 preferably are formed by heat-sealing the two plys of the airbag together having a peripheral seam in the shape indicated by the cross-sectional hatching. Techniques for doing this are well known in the art.

Obviously, still further modifications of my invention will occur to those skilled in the art. Accordingly it is desired that the present invention be limited only by the true spirit and scope of the appended claims.

I claim:

1. In an inflatable article having an integral valve; comprising at least a pair of sheets bonded together along their periphery in the shape of the article, said valve being joined to and extending from said periphery and being extensions of said sheets, the outer housing of the valve being formed by said sheet extensions sealed together along side edges to leave outer edges of the sheets unattached and forming an opening through which the article is inflated; and at least one of said outer edges being folded inwardly of and positioned within said outer housing to provide a flap responsive to the pressure of the fluid in the article to maintain the flap in a position effective to seal the valve wherein the improvement comprises: means disposed on the surface of said at least one flap to bias the flap into sealing position, said biasing means comprising a thin layer of a tacky, grease-like substance, and means for maintaining an adequate supply of said substance in the vicinity of said flap comprising a member extending transversely inwardly of said valve to form a recess for receivably storing said tacky, grease-like substance interiorly of said valve.

2. The invention of claim 1 wherein said substance comprises a silicone-based grease compound.

3. The invention of claim 1 wherein said thin layer of said substance adheres to said flap surface and the inner wall surface of said valve housing opposite the wall surface of said valve housing which includes the fold forming said flap.

4. The invention of claim 1 wherein the unattached outer edges of said sheets are each folded inwardly to form a pair of confronting flaps positioned within said valve housing and said thin layer of a tacky, grease-like substance adheres to said confronting flaps.

* * * * *